United States Patent
Baker, Jr.

[19]

[11] Patent Number: 6,035,223
[45] Date of Patent: Mar. 7, 2000

[54] METHOD AND APPARATUS FOR DETERMINING THE STATE OF AN OXIMETRY SENSOR

[75] Inventor: Clark R. Baker, Jr., Castro Valley, Calif.

[73] Assignee: Nellcor Puritan Bennett Inc., Pleasanton, Calif.

[21] Appl. No.: 08/974,274

[22] Filed: Nov. 19, 1997

[51] Int. Cl.[7] .................................................. A61B 5/00
[52] U.S. Cl. .......................... 600/323; 600/300; 600/310
[58] Field of Search .................... 600/310, 322, 600/323, 331, 336, 300, 301, 309; 356/41; 128/920, 925

[56] References Cited

U.S. PATENT DOCUMENTS

| | | | |
|---|---|---|---|
| 4,603,700 | 8/1986 | Nichols et al. | 600/331 |
| 5,503,148 | 4/1996 | Pologe et al. | 600/323 |
| 5,645,060 | 7/1997 | Yorkey | 128/633 |
| 5,662,106 | 9/1997 | Swedlow et al. | 128/633 |

*Primary Examiner*—Eric F. Wincker
*Attorney, Agent, or Firm*—Beyer & Weaver, LLP

[57] ABSTRACT

A method for determining whether a sensor is coupled to a tissue sample is described. The sensor is operable to generate a detector signal indicative of absorption of electromagnetic radiation by the tissue sample. A plurality of metric values corresponding to the detector signal are generated. A neural net is employed with the metric values to determine whether the sensor is coupled to the tissue sample.

22 Claims, 3 Drawing Sheets

METHOD AND APPARATUS FOR DETERMINING THE STATE OF AN OXIMETRY SENSOR

BACKGROUND OF THE INVENTION

The present invention relates generally to pulse oximetry systems and specifically to a method and apparatus for determining whether an oximetry sensor is properly in contact with a patient.

Pulse oximeters measure and display various blood flow characteristics including but not limited to the oxygen saturation of hemoglobin in arterial blood. Oximeters transmit light through blood perfused tissue such as a finger or an ear, and photoelectrically sense the absorption of light in the tissue. The light passed through the tissue is selected to be of one or more wavelengths that are absorbed by the blood in an amount representative of the amount of a blood constituent present in the blood. The amount of light absorbed is then used to calculate the concentration of the blood constituent.

A wide variety of oximeter sensors are available from a number of manufacturers which provide the interface between the patient and the oximeter. Oximeter sensors typically include two LEDs of different wavelengths which alternately transmit light into the tissue, and a detector for receiving the light after passing through the tissue. In processing the detector signal received from the sensor, it is important that the oximeter have accurate information regarding the state of the sensor. That is, the oximeter must be able to reliably determine whether the sensor is on or off the patient. If the oximeter receives inaccurate information regarding the state of the sensor, it may issue false alarms regarding the patient's health, or more seriously, may fail to report an emergency condition when one exists.

Previous generation oximeters attempt to detect the SENSOR OFF condition. However the reliability of these detection schemes is not well documented. One oximetry system addresses the problem by providing for a timeout period during which either no pulses or pulses unacceptable for oximetry calculations are detected. If a timeout occurs, it is assumed that the sensor may not be in contact with the patient, and the oximetry system ceases to display saturation and pulse rate. However, recent oximetry algorithms are more robust in that they are able to use or selectively ignore previously unusable data, e.g., data corrupted by motion artifact, during the determination of blood constituent concentrations instead of reporting a pulse timeout. As a result, the pulse timeout algorithm is no longer suitable for determining whether the sensor remains in contact with the patient.

In addition, the pulse qualification of one previous embodiment relied on a decision tree implemented using ad hoc and non-uniform logic. The thresholds or coefficients of such algorithms were typically selected manually resulting in a sub-optimal separation of the regions of interest in the input space. Moreover, such decision trees do not typically represent non-linear relationships.

It is therefore desirable to provide a reliable method for determining whether a pulse oximeter sensor is in proper contact with a patient.

SUMMARY OF THE INVENTION

According to the present invention a method and apparatus are provided by which it can be reliably determined whether a pulse oximeter sensor is in sufficient contact with a patient to allow determination of the concentration of a blood constituent such as, for example, oxyhemoglobin. The present invention employs an artificial neural net to discriminate between two conditions designated the SENSOR ON and SENSOR OFF conditions. The neural net receives a plurality of input metrics which are representative of characteristics of the signals received from the detector in the oximeter sensor. These input metrics have been designed and selected to be relatively insensitive to absolute light levels, the current oxygen saturation value, the pulse rate, changes in both the oxygen saturation value and pulse rate, motion artifact, dichrotic notches, arrhythmias, and respiratory artifact. The neural net is trained using a large database containing a wide variety of patient and SENSOR OFF conditions. The training of the neural net involves a process of data reduction by which relationships in the data are identified and represented as a small number of scalar metrics. Each of the input metrics received by the neural net of the present invention is conditioned to isolate different behaviors which are highly specific to the SENSOR OFF and SENSOR ON conditions. The input metrics to the neural net represent data within a time span which is sufficiently short to ensure an acceptable response time and sufficiently long to avoid noisy and erratic behavior.

Thus, the present invention provides methods and apparatus for determining whether a sensor is coupled to a tissue sample. The sensor is operable to generate a detector signal indicative of a parameter associated with the tissue sample. A plurality of metric values corresponding to the detector signal are generated. A filter is employed with the metric values to determine whether the sensor is coupled to the tissue sample. The filter is operable to perform data reduction based on dependencies among the metric values. According to a specific embodiment, the sensor is operable to generate a detector signal indicative of absorption of electromagnetic radiation by the tissue sample. A plurality of metric values corresponding to the detector signal are generated. A neural net is employed with the metric values to determine whether the sensor is coupled to the tissue sample.

A further understanding of the nature and advantages of the present invention may be realized by reference to the remaining portions of the specification and the drawings.

DESCRIPTION OF SPECIFIC EMBODIMENTS

Figure 1:
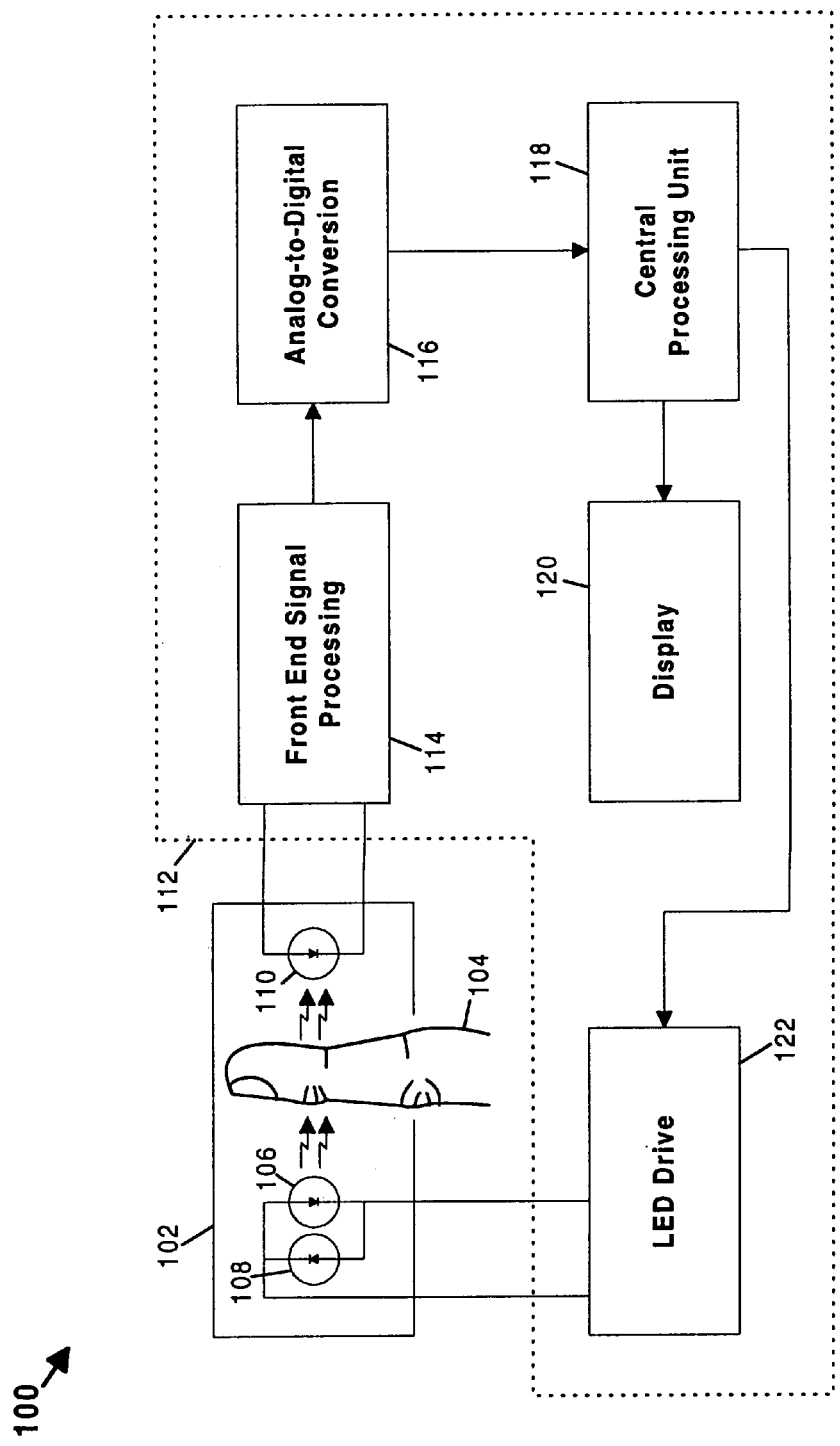
FIG. 1 is a block diagram of an oximetry system.

FIG. 1 is a block diagram of an oximetry system 100 for use with the present invention. An oximetry sensor 102 is attached to a blood perfused tissue sample such as a patient's finger 104. Red and infrared (IR) LEDs 106 and 108 alternately transmit Red and IR light toward finger 104. Detector 110 receives the Red and IR light transmitted through finger 104. Sensor 102 is connected to oximeter 112 which receives and processes the signal from detector 110, and which also provides the drive signal to LEDs 106 and 108. The detector signal is received by front end signal processing circuitry 114 which demodulates the alternately transmitted Red and IR light received by detector 110, cancels ambient light, and includes fixed and variable hardware gain stages prior to digitization. The processed analog signal is converted to a digital signal by analog-to-digital conversion circuitry 116 and sent to central processing unit (CPU) 118 for computation of estimates of the oxygen saturation of hemoglobin in the arterial blood and the pulse rate. CPU 118 also determines whether sensor 102 is in contact with finger 104 as described below. The calculated oxygen saturation and pulse rate values are then sent to display 120. CPU 118 also controls LED drive circuitry 122 which provides the drive signals for LEDs 106 and 108. One example of an oximetry system for use with the present invention is described in commonly assigned, copending U.S. Application Ser. No. 08/660,510 for METHOD AND APPARATUS FOR ESTIMATING PHYSIOLOGICAL PARAMETERS USING MODEL-BASED ADAPTIVE FILTERING filed on Jun. 7, 1996, which was based on Provisional Application No. 60/000,195 filed on Jun. 14, 1995, the entire specifications of which are incorporated herein by reference.

Figure 2:
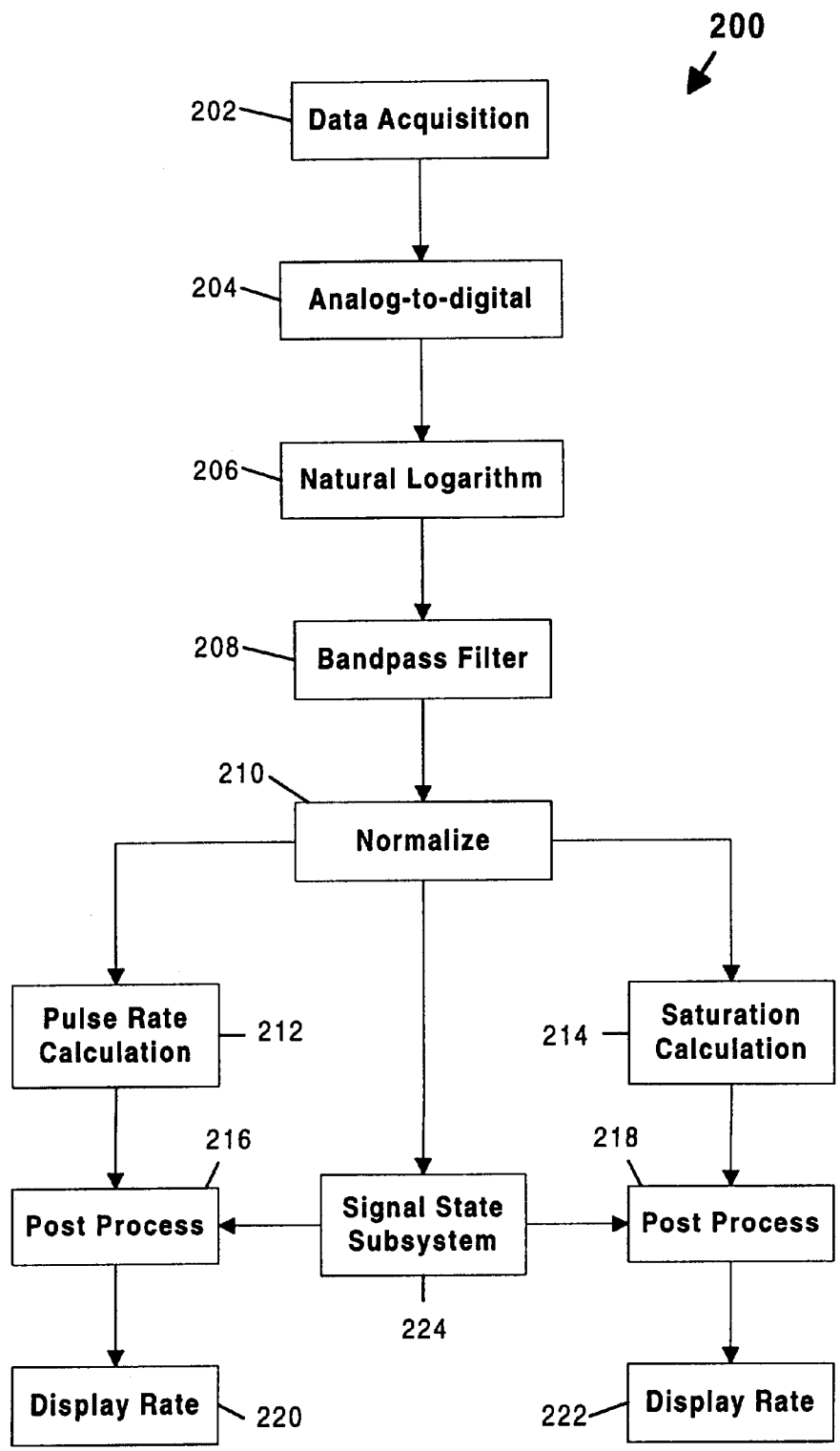
FIG. 2 is a process flow diagram for the oximetry system of FIG. 1.

FIG. 2 is a process flow diagram 200 which describes the operation of the oximetry system 100 in greater detail. Data acquisition 202 may be achieved using a wide variety of available sensors such as, for example, sensor 102 of FIG. 1. The acquired data are digitized at an appropriate sample rate (step 204), and the natural logarithm of the digitized Red and IR waveforms is taken (step 206). The resulting data are then bandpass filtered (step 208) with an infinite impulse response filter (IIR) having a high pass cutoff at 0.5 Hz and a low pass roll off from 10 to 20 Hz. The data are then normalized (step 210). Normalization down-weights large pulse amplitudes so that each pulse has roughly the same average amplitude. As a result, samples exhibiting large amounts of motion artifact are down-weighted, thus de-emphasizing outliers.

The filtered and normalized data are then employed for calculation of the pulse rate and oxygen saturation (steps 212 and 214). The values yielded by these process steps are both subjected to post processing (steps 216 and 218) which uses available metrics with regard to the calculated values to determine their reliability and whether and how they should be displayed. The respective values are then displayed (steps 220 and 222). The digitized, filtered and normalized data are also provided to signal state subsystem 224 which, using a plurality of metrics, determines whether the oximetry probe is properly attached to the patient. The output of signal state subsystem 224 is provided to the post processing for both the oxygen saturation and pulse rate algorithms (i.e., steps 216 and 218) so that an appropriate decision may be made as to whether and how to display the current values reported by those algorithms. The operation of signal state subsystem 224 and its effects on the pulse rate and oxygen saturation algorithms will be discussed in greater detail below with reference to FIG. 3.

Figure 3:
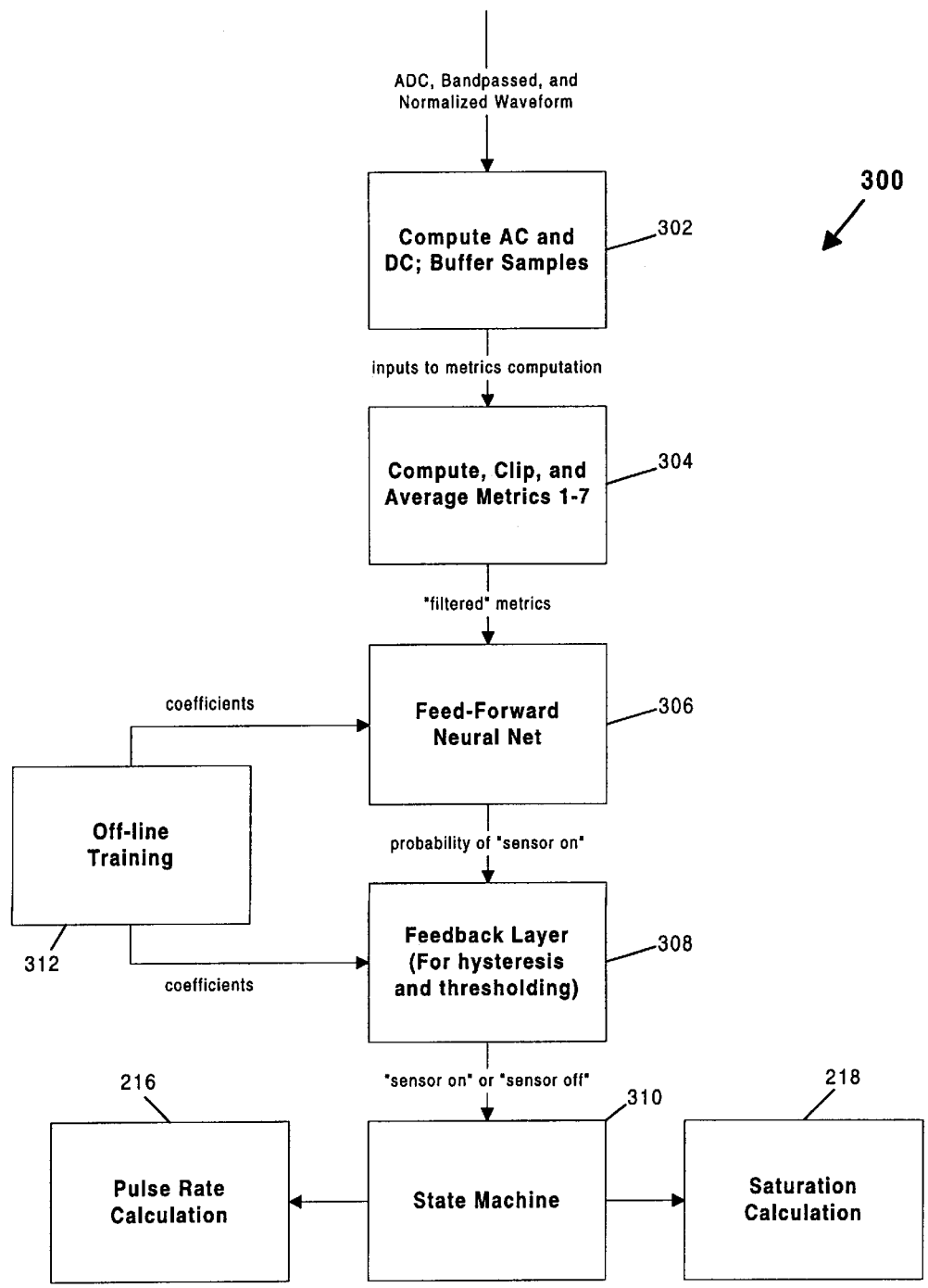
FIG. 3 is a process flow diagram illustrating the operation of a specific embodiment of the invention.

FIG. 3 is a process flow diagram 300 illustrating the operation of signal state subsystem 224 of FIG. 2. The digitized, filtered and normalized data are received at process step 302 where the AC and DC components of the Red and IR waveforms are computed and buffered. The AC and DC components of the Red and IR waveforms are used as inputs to metric computation 304 in which the individual metrics are computed, clipped, and averaged yielding seven "filtered" metrics used by feed-forward neural net 306 to determine whether the oximetry sensor is properly connected to the patient and to generate a value representing the probability thereof.

An artificial neural network (ANN), e.g., neural net 306, is a data processing architecture that is modeled on principles exhibited in natural or biological neural networks. Artificial neural networks are often used to represent or process nonlinear functions applied to large data sets. Artificial neural network engines can be implemented in software, hardware (using parallel processing architectures) or a combination of both. Artificial neural networks are well-suited for detecting trends or patterns in data.

Artificial neural networks are represented symbolically as an interconnected network of nodes arranged in a specific topology or configuration. Links between nodes represent dependencies between nodes and have weights associated with each link representing the strengths of the dependencies. Artificial neural networks typically have an input layer, hidden or processing layers, and an output layer. The links between nodes are adjusted for specific tasks by training of the network, which involves exposing the network to representative data sets to be processed. Output from the network are compared to desired results and corresponding adjustments are made to reduce any discrepancies between the desired output and the actual output. The seven metrics employed by the present invention as inputs to neural net 306 quantify several aspects of the behavior of the Red and IR data over the previous several seconds. The nature of each of the seven metrics is described below in greater detail.

A feedback layer 308 provides a threshold for comparison to the probability value received from neural net 306, and yields either a SENSOR ON or a SENSOR OFF indication to state machine 310. Feedback layer has hysteresis built in. The coefficients for both neural net 306 and feedback layer 308 are determined by an off-line training algorithm 312 which is responsible for finding and optimizing the relationships between the inputs to these layers and the desired outputs. The training algorithm will be described below in greater detail.

State machine 310 delivers one of five Signal State indications to the post processing subsystems 216 and 218 for both the pulse rate and oxygen saturation algorithms thereby recommending appropriate actions for these subsystems. The possible actions for the post-processing subsystems are updating the oxygen saturation and pulse-rate outputs, holding the current oxygen saturation and pulse-rate outputs, or clearing the oxygen saturation and pulse-rate outputs. According to a specific embodiment, the oximeter displays appropriate audio or visual indications based on the Signal State output. The possible Signal State indications are:

PULSE The oximetry sensor is most likely
PRESENT: connected to the patient and appears to be acquiring a pulse.
DISCONNECT: A Valid sensor is not connected to the oximeter.
PULSE LOST: A pulse was previously acquired by the oximeter and was subsequently lost while the sensor was connected to the oximeter and did not appear to have fallen off the patient. The term "PULSE LOST" refers to the complete absence of a pulse or a dramatic diminution of the pulse amplitude as seen by the oximetry sensor.
SENSOR OFF: The sensor is probably not on the patient, or may be seeing an unacceptable amount of interference. The sensor is connected to the oximeter. This state is normally entered when the Signal State has been SENSOR MAYBE OFF for a continuous period of seven seconds. This state is not entered subsequent to entering the PULSE LOST state.
SENSOR MAYBE OFF: A seven-second waiting period prior to entering the SENSOR OFF state. The neural net is used to determine when this and the subsequent SENSOR OFF state should be entered and exited. This state is not entered subsequent to entering the PULSE LOST state.

The Signal State subsystem provides two forms of feedback to the oxygen saturation and pulse-rate calculations:

1) Samples which occur while the Signal State is not PULSE PRESENT or SENSOR MAYBE OFF are not used to calculate oxygen saturation or pulse rate.
2) Appropriate subsystems are reinitialized:
   a) When the sensor is reconnected to the oximeter
   b) When the Signal State transitions to PULSE PRESENT from SENSOR OFF or PULSE LOST.

At every sample, the Signal State subsystem determines the Signal State by analyzing several metrics computed from the IR and Red analog-to-digital converted (ADC), normalized, and derivative filtered values, in conjunction with the system gains and flags indicating the validity of these values. A Sensor Valid flag indicates whether the sensor is connected to the oximeter. A large, sudden drop in IR percent modulation unaccompanied by a simultaneous change in IR light level (as represented by the digitized IR waveform corrected for gain and LED settings) indicates that the pulse has been lost and the sensor is still on the patient. The neural net receives the input metrics defined below and determines whether the sensor is off the patient.

As discussed above, the Signal State subsystem uses a neural net to determine whether the sensor is off the patient. The inputs to the neural net are metrics, defined below, which quantify several aspects of the behavior of the IR and Red ADC values over a period of several seconds. The neural net is trained using the Levenberg-Marquardt back-propagation method. The training algorithm is responsible for finding and optimizing the relationships between the neural net's inputs and its desired output. The trained neural net is implemented as an array of dot products and a few transcendental functions. Retraining only requires an update of the neural net's coefficients, leaving the code unchanged. The neural net is trained, optimized and evaluated on large databases containing a wide range of patient and SENSOR OFF conditions. A large subset of these databases was designated as a "test database", for which the SENSOR ON or SENSOR OFF condition was manually determined. The neural net and its input metrics are trained, designed, and evaluated to maximize the sensitivity, specificity, and responsivity of the Signal State Subsystem.

A human can reliably determine whether the sensor is off by manual inspection of the IR and Red waveforms. For example, large, sudden changes in the levels of the digitized waveforms (corrected for gain and LED changes) are an indication that the sensor has come off or has recently been applied. Extremely poor crosscorrelation of the IR and Red bandpassed and normalized waveforms, is an indication that the sensor is off, although moderately poor correlation may be caused by motion. Very tiny modulations in the bandpassed waveforms, with or without slow linear drifts in the DC level, are also indications that the sensor is off the patient. The consistency of the size, shape, and period of the "pulses" in the AC-coupled waveforms is a further indication of whether they are due to a human pulse. A human will take into account factors that can change as a result of normal human physiology or sensor application. These include absolute light levels (as represented by the levels of the digitized waveforms corrected for gain and LED settings), gradual changes in light level due to blood pressure changes, changes in oxygen saturation, pulse rate, or pulse amplitude, as well as motion, dichrotic notches, arrhythmias, and respiratory artifact.

The human eye automatically performs data reduction when the IR and Red waveforms are manually inspected to determine whether the sensor is off. Design and training of the neural net of the present invention for this purpose also requires data reduction. In this context, the data reduction operation involves identifying relationships in the data that, in combination, are likely to produce a reliable SENSOR OFF indication, and representing these as a small number of scalar metrics. According to a specific embodiment, the neural net receives 7 inputs metrics, each conditioned to isolate different behaviors that are highly specific to the SENSOR OFF or SENSOR ON conditions. These metrics represent data occurring within a relatively brief time span corresponding to the desired response time for the neural net. If the metrics represent data over too brief a window with respect to this response time, the neural net's output is noisy and erratic. If, on the other hand, the metrics represent data from too long a window, the neural net responds too slowly. Several input metrics are based on changes in the digitized IR value which is corrected for front-end gain and LED drive changes to minimize the effect of such changes on the neural net's behavior.

Metric 1 is the average IR AC amplitude. The unaveraged IR AC amplitude is the difference between the maximum and minimum digitized IR level over an appropriate period. This metric is sensitive to rapid changes in light absorption. The IR channel is used because the IR light level is less affected by large oxygen saturation changes than the Red light level is. Because light level can change drastically when the sensor comes off, this max-min difference is scaled in dB. This metric is then averaged using a single-pole IIR filter with an appropriate time constant. This averaging makes the metric less sensitive to irregular pulse amplitudes that occur during arrhythmias, and to zero modulations that could be computed during gain and LED adjustments. When this average is increasing, arithmetic averaging is used. When the average metric is decreasing, harmonic averaging is used. This metric will be very large when the sensor falls off or is reapplied, and harmonic averaging assures a faster convergence time once the sensor is applied. According to specific embodiments, the averaged IR AC modulation may be explicitly limited to a maximum value. This limits the range of this metric over which the neural net must be trained, and reduces convergence time after the sensor is reapplied.

Very high or very low values of Metric 1 are likely indicators that the sensor is off the patient. When the sensor falls off or is reapplied, this metric should be very high. The response time of the IIR should be short enough for this metric to settle down to a "normal" looking value within a reasonable period of time. The period for computing this metric should be adequate for low pulse rates, i.e., long enough to encompass a substantial portion of the pulse amplitude. In any event, the Metric 1 estimate will not be any more variable due to low pulse rates than it is during arrhythmias which are also classified correctly by the neural net.

Metric 2 is the relative variability of the IR AC amplitude. That is, a variance metric is computed for the unaveraged IR AC amplitude described above. The difference in the unaveraged IR AC amplitude (already in units of dB) between consecutive computation periods is squared, and this squared difference is averaged with a single-pole IIR filter with an appropriate time constant, then the square root is taken. When this average is increasing, arithmetic averaging is used. When the average is decreasing, harmonic averaging is used. This metric is very large when the sensor falls off or is reapplied, and harmonic averaging assures a faster convergence time once the sensor is applied.

According to specific embodiments, this averaged squared difference may be explicitly limited to a maximum value. This limits the range of this metric over which the neural net must be trained, and reduces convergence time after the sensor is reapplied. Finally, the limited averaged squared difference is divided by the averaged IR AC amplitude, i.e., Metric 1. Because Metric 2 is dependent on Metric 1, both metrics use the same response time for their IIR filters. Metric 2 represents the consistency of the pulse size over the past several seconds. High values of this metric may indicate an arrhythmia or a SENSOR OFF condition. Low values indicate a high probability that the sensor is on the patient.

Metric 3 is based on the degree to which the IR and Red AC-coupled waveforms are correlated. This "uncorrelation" metric is computed from IR and Red waveforms that have been bandpass filtered, normalized, and whitened, where the whitening filter is a first difference filter. A first difference filter is used to downweight lower frequencies because motion artifact will typically occur at frequencies lower than the pulse rate. This is particularly the case with infants, where motion artifact is most common.

The formula for the "uncorrelation" metric is:

$$\sqrt{\frac{\sum_{i=0}^{M-1}(Red_{t-i} - IR_{t-i}R)^2}{\sum_{i=0}^{M-1} Red_{t-i}^2}}$$

where $$R = \frac{\sum_{i=0}^{M-1} IR_{t-i} Red_{t-i}}{\sum_{i=0}^{M-1} IR_{t-i}^2}$$

where t is in samples and M is set to define an appropriate computation period. Metric 3 is zero in case of division by zero, if R is zero or if the expression under the square root is zero. It ranges from zero to one.

The metric is then averaged with a single-pole IIR filter with an appropriate time constant because large transient motion artifacts may cause a sudden change in its value. The extra averaging keeps the neural net from spuriously reporting SENSOR OFF due to these transients. The likelihood of SENSOR OFF increases monotonically with this metric.

Metric 4 is the variability of the IR DC light level. The average valid IR light level over some appropriate period is computed. This DC estimate is sensitive to low frequency changes in light absorption. The IR channel is used because the IR light level is less affected by large oxygen saturation changes than the Red light level is. A variance metric is then computed for this IR DC term. The difference in the IR DC values, in dB, between consecutive computation periods is squared, and this squared difference is averaged with a single-pole IIR filter with an appropriate time constant. When this average is increasing, arithmetic averaging is used. When the average is decreasing, harmonic averaging is used. This metric is very large when the sensor falls off or is reapplied, and harmonic averaging assures a faster convergence time once the sensor is applied. The DC difference term is in units of dB because light level can vary drastically when the sensor comes off.

The variance metric is the square root of this averaged squared difference. According to specific embodiments, the averaged squared difference may be explicitly limited to a maximum value. This limits the range of this metric over which the neural net must be trained, and reduces convergence time after the sensor is reapplied.

Metric 4 therefore represents the variability of the DC light level over the past several seconds. High values of this metric should either indicate a SENSOR OFF condition with ongoing sensor motion, or that the sensor has just been reapplied and the metric is still converging. The computation period for this metric should be adequate for low pulse rates, i.e., long enough to encompass a substantial portion of the pulse. Small changes in Metric 4 due to the pulse amplitude should be no larger than those due to respiratory artifact, which is also classified correctly by the neural net.

Metric 5 is the bias or slope of the IR DC light level. According to specific embodiments, the range of this may be explicitly limited, thereby limiting the range over which the neural net must be trained, and reducing convergence time after the sensor is reapplied. According to other specific embodiments, the absolute value of the metric may be taken, thereby further limiting the range over which the neural net must be trained. The sign of the DC slope is not believed to correlate to the likelihood that the sensor is off, either by itself or in conjunction with the neural net's other input metrics. Very high values of Metric 5 may indicate that the sensor has just fallen off or been reapplied. Moderately high values may indicate that the sensor is on the patient and a large baseline shift is occurring for some physiological reason. In this latter case, Metric 1 would probably also increase and the combined behavior of Metric 1 and Metric 5 would indicate that the sensor is still on the patient.

Metric 6 is representative of the pulse shape. The characteristic asymmetry of a typical human pulse (as represented, for example, by the IR waveform) causes the derivative of the digitized waveform to have a negative skew. According to specific embodiments, this derivative value is averaged over a small number of samples to reduce high-frequency noise that is not indicative of whether the sensor is on or off the patient. Non-pulsatile signals are typically symmetric, with an average skew of zero. The equation for skewness is:

$$\frac{n \sum (x_i - \bar{x})^3}{(n-1)(n-2)\sigma^3}$$

where n is the sample count and σ is the standard deviation of x. Normalizing by $\sigma^3$ makes this metric scale-independent. A first difference filter is used to downweight lower frequencies because motion artifact will typically occur at frequencies lower than the pulse rate. The equation for σ is:

$$\sigma = \sqrt{\frac{n(\sum x_i^2) - (\sum x_i)^2}{n(n-1)}} = \sqrt{\frac{\sum (x_i - \bar{x})^2}{(n-1)}}$$

where n is the number of Valid IR Derivative samples that occurred over an appropriate computation period, and the summations are computed over those samples. If n is less than 3, or if the expression under the square root sign is not positive, skew is set to zero. According to specific embodiments, if n is too small to represent a significant portion of a pulse, skew is also set to zero. According to specific embodiments, the range of the skew is explicitly limited, and then averaged with a single-pole IIR filter with an appropriate time constant. The averaging period should assure that Metric 6 is not unduly biased due to being calculated over a non-integral number of pulses.

Metric 7, harmonicity, is computed from the IR waveform after it has been bandpass filtered, normalized, and whitened, where the whitening filter is a first difference filter. The metric searches for the maximum autocorrelation of this IR waveform over the range of 20 to 250 beats per minute (BPM) Autocorrelation, $A_n$ is defined as:

$$\frac{\sum_{i=0}^{M-1} IR_{t-i} IR_{t-i-n}}{\sum_{i=0}^{M-1} IR_{t-i}^2} = \frac{D_n}{D_0}$$

where t is in samples, n represents a delay in samples, and M is set to define an appropriate computation period. $A_n$ is computed using samples stored in an M-sample circular buffer. Note that $D_0$ only needs to be computed once for all values of n. According to a specific embodiment, instead of making a compute-intensive calculation of $A_n$ for all n, the algorithm makes several rough approximations of the pulse rate, picks the highest $A_n$, then maximizes $A_n$ using a Newton search.

Metric7 is set to the highest $A_n$ computed by this algorithm, but not less than zero. At low pulse rates, when M is not an integral multiple of the pulse interval, the maximum autocorrelation is somewhat less than 1.0, but still high enough to keep harmonic signals from being classified as SENSOR OFF.

Because, in reality, we do not see continuous, uninterrupted IR and Red data streams, several exceptions are implemented due to events that interrupt the data streams. For example, during sensor disconnects, Metrics 1–7 are explicitly set to zero, so that data representing sensor disconnects can be easily identified and ignored when training the neural net. It will be understood that a variety of other exceptions may be necessary to account for other conditions depending upon the performance level desired.

The neural net of the present invention is trained as a feed-forward network with a ten-node hidden layer and a single-node output layer. All nodes are fully connected, and have associated bias inputs. The hidden layer therefore contains (7+1)*10=80 tunable coefficients, and the output layer contains (10+1)*1=11 tunable coefficients. The jth neuron in a layer has n inputs, $x_{1..n}$, n weights, $w_{1,j..n,j}$, a bias, $b_j$, a transfer function F(), and an output, $y_j$:

$$y_j = F\left(b_j + \sum_{i=1}^{n} w_{i,j} x_i\right)$$

All nodes in a layer receive the same inputs, although they have different weights and biases. The inputs to the hidden layer are the seven input metrics described above. The inputs to the output layer are the outputs of the ten hidden nodes in the hidden layer. The neural net's training goal is to accurately output the probability (between 0 and 1) that the sensor is off given the values of the neural net's input metrics. To do this, the neural net's hidden nodes collectively allow the neural net to map the "boundary" of the region of this input space in which the SENSOR ON data are believed to lie. Ten hidden nodes are believed to be near-optimal, providing a reasonable number of nodes for mapping the neural net's seven-dimensional input space, while being low enough to allow the neural net's performance to converge quickly during retraining sessions. Constraints on the values of neural net's input metrics limit the input space that must be mapped by the neural net. This allows the finite number of hidden nodes to map this constrained input space more thoroughly than if the input space was not explicitly constrained.

Because the neural net's training goal is to output a probability between 0 and 1, the output node and all hidden nodes use the logarithmic sigmoid, or logsig(), transfer function, which compresses an infinite signed input range into an output range of 0–1. The formula for the logsig() transfer function is:

$$\text{logsig}(x) = (1 + e^{-x})^{-1}$$

In order to prevent the exponential in this equation from over or underflowing, x should be constrained to appropriate limits.

Although the neural net's automated training algorithm trains a feed-forward network, according to a specific embodiment of the invention, the neural net implemented in the Signal State subsystem adds a feedback layer to keep its output stable and minimize SENSOR ON or SENSOR OFF classification errors (e.g., feedback layer 308 of FIG. 3). Specifically, the formula for the neural net's single output node, y, is changed to:

$$y_t = \text{logsig}(Ax_t + Bz_{t-1} + C) \quad z_t = Dy_t + (1-D)z_{t-1}$$

where the feedback coefficients, A, B, C, and D, are manually tuned after training the feed-forward network. The feed-forward network is equivalent to setting A=1, B=0, and C=0. The value of A determines how much the feed-forward portion of the network affects the current output. The value of B affects how much hysteresis is applied to the network. The C coefficient serves as an extra bias to compensate for the fact that $y_t$, and therefore $z_t$, is always positive. The value of C determines the balance between missed and false SENSOR OFF reports produced by the neural net. The value of D determines the response time for z, and therefore affects the response time of the feedback stage. The values of A, B, C, and D are determined empirically.

Given a neural net output of 0.5 as the decision point for reporting SENSOR ON or SENSOR OFF, the coefficients are set so that the value of $x_t$ that produces a neural net output of approximately 0.5 is the same with and without feedback. With no feedback, the logsig() output neuron outputs 0.5 when $x_t$=0. The relationship between B and C which produces a neural net output of 0.5 for a constant value of $x_t$=0 is:

$$x_t = Ax_t + Bz_{t-1} + C = 0$$
$$y_t = y_{t-1} = z_t = z_{t-1} = 0.5$$
$$0.5B + C = 0$$
$$C = -0.5B$$

The above formula only approximates the optimal ratio of B and C for any given database and coefficient set.

While the invention has been particularly shown and described with reference to specific embodiments thereof, it will be understood by those skilled in the art that changes in the form and details of the disclosed embodiments may be made without departing from the spirit or scope of the invention. For example, the present invention has been described with reference to a particular oximetry system. It will be understood, however, that the present invention may be implemented with a wide variety of oximetry systems.

For that matter, the techniques described herein may be applied in a wide variety of setting to determine whether a sensor is coupled to a tissue sample. In addition, the present invention has been described with regard to the use of a neural net. It should be noted, however, that other types of algorithms are suitable for performing the data reduction necessary to make appropriate decisions based on a given set of input metrics. That is, a neural net's training procedure is an example of a repeatable method for directly or indirectly determining linear or non-linear boundaries that maximally separate multi-dimensional regions of interest, or for approximating arbitrary functions of multiple inputs. Other kinds of algorithms or filters that may be employed with the present invention include, but are not limited to, (1) Genetic Algorithms, or (2) Linear discrinant techniques including, for example, (a) Multivariate regression techniques, (b) Nearest-neighbor techniques (distance metrics may include Euclidean distance or Mahalonobis distance), and (c) Bayesian detection (requires that regions be statistically characterized in advance). Similarly, the invention has been described with reference to the use of red and infrared frequencies to illuminate a tissue sample. Obviously, the present invention is not limited to these frequency ranges but may be employed with any combination of radiation frequencies.

Finally, it will be understood that any of the metrics described herein, e.g., the pulse shape metric, may be computed in a variety of ways without departing from the scope of the invention. Therefore, the scope of the invention should be determined with reference to the appended claims.

What is claimed is:

1. A method for determining whether a sensor is coupled to a tissue sample, the sensor being operable to generate a detector signal indicative of absorption of electromagnetic radiation by the tissue sample, the method comprising:

generating a plurality of metric values corresponding to the detector signal, each of the metric values guantifying a behavior of the detector signal which is correlated with whether the sensor is coupled to the tissue sample:

inputting the plurality of metric values to a neural net, performing data reduction with the neural net based on dependencies among the metric values, and generating a probability value indicative of whether the sensor is coupled to the tissue sample; and determining whether the sensor is coupled to the tissue sample by referring to the probability value.

2. The method of claim 1 wherein generating the plurality of metric values comprises:

performing analog signal processing on the detector signal;

after the analog signal processing, converting the detector signal to a digital signal;

generating AC and DC components of the digital signal corresponding to AC and DC components of the detector signal; and generating the plurality of metric values using the AC and DC components of the digital signal.

3. The method of claim 2 further comprising taking the natural logarithm of the digital signal.

4. The method of claim 2 further comprising bandpass filtering the digital signal.

5. The method of claim 2 further comprising normalizing the digital signal.

6. The method of claim 2 wherein the detector signal comprises a first portion corresponding to electromagnetic radiation of a first frequency, and a second portion corresponding to electromagnetic radiation of a second frequency, selected ones of the metric values being generated using AC and DC components of the digital signal corresponding to the first portion of the detector signal.

7. The method of claim 1 wherein the detector signal comprises an infrared portion corresponding to infrared radiation and a red portion corresponding to red radiation, and wherein generating the plurality of metric values comprises generating infrared AC and DC component signals corresponding to the infrared portion of the detector signal, and red AC and DC component signals corresponding to the red portion of the detector signal.

8. The method of claim 7 wherein the plurality of metric values comprises the average amplitude of the infrared AC component signal.

9. The method of claim 8 wherein the average amplitude is determined using an infinite impulse response filter.

10. The method of claim 7 wherein the plurality of metric values comprises the variability of the amplitude of the infrared AC component signal.

11. The method of claim 7 wherein the plurality of metric values comprises the degree to which the infrared and red portions of the detector signal are correlated.

12. The method of claim 11 wherein the degree to which the infrared and red portions of the detector signal are correlated is determined with reference to a digitized and normalized portion of the detector signal.

13. The method of claim 7 wherein the plurality of metric values comprises the variability of the amplitude of the infrared DC component signal.

14. The method of claim 7 wherein the plurality of metric values comprises the slope of the infrared DC component signal.

15. The method of claim 7 wherein the plurality of metric values comprises a pulse shape metric which is reflective of a pulse shape associated with the infrared portion of the detector signal.

16. The method of claim 7 wherein the plurality of metric values comprises a maximum autocorrelation value corresponding to a digitized and normalized portion of the detector signal.

17. The method of claim 1 further comprising training the neural net to determine whether the sensor is coupled to the tissue sample using a database of previously recorded sensor data.

18. The method of claim 17 wherein the neural net comprises a plurality of processing nodes each having at least one coefficient associated therewith, and wherein training the neural net comprises determining values for each of the coefficients.

19. The method of claim 18 wherein training the neural net comprises mapping an input space defined by the plurality of metric values.

20. The method of claim 19 wherein the plurality of metric values are explicitly constrained during the mapping of the input space.

21. At least one computer readable medium containing program instructions for determining whether a sensor is coupled to a tissue sample, the sensor being operable to generate a detector signal indicative of absorption of electromagnetic radiation by the tissue sample, said at least one computer readable medium comprising:

computer readable code for generating a plurality of metric values corresponding to the detector signal, each of the metric values quantifying a behavior of the detector signal which is correlated with whether the sensor is coupled to the tissue sample;

computer readable code for inputting the plurality of metric values to a neural net;

computer readable code for performing data reduction with the neural net based on dependencies among the metric values, and generating a probability value indicative of whether the sensor is coupled to the tissue sample; and computer readable code for determining whether the sensor is coupled to the tissue sample by referring to the probability value.

22. A method for determining whether a sensor is coupled to a tissue sample, the sensor being operable to generate a detector signal indicative of a parameter associated with the tissue sample, the method comprising:

generating a plurality of metric values corresponding to the detector signal, each of the metric values quantifying a behavior of the detector signal which is correlated with whether the sensor is coupled to the tissue sample;

inputting the plurality of metric values to a filter;

performing data reduction with the filter based on dependencies among the metric values, and generating a probability value indicative of whether the sensor is coupled to the tissue sample; and determining whether the sensor is coupled to the tissue sample by referring to the probability value.

* * * * *